(12) United States Patent
Kim

(10) Patent No.: US 10,652,988 B2
(45) Date of Patent: May 12, 2020

(54) MOBILE X-RAY APPARATUS INCLUDING A BATTERY MANAGEMENT SYSTEM

(71) Applicant: SAMSUNG ELECTRONICS CO., LTD., Suwon-si (KR)

(72) Inventor: Myeong-je Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/977,455

(22) Filed: May 11, 2018

(65) Prior Publication Data

US 2018/0270938 A1 Sep. 20, 2018

Related U.S. Application Data

(63) Continuation of application No. 15/391,957, filed on Dec. 28, 2016, now Pat. No. 9,992,853.

(30) Foreign Application Priority Data

Aug. 3, 2016 (KR) .................. 10-2016-0099134
Dec. 28, 2016 (KR) .................. 10-2016-0181361

(51) Int. Cl.
*H05G 1/08* (2006.01)
*H05G 1/10* (2006.01)
(Continued)

(52) U.S. Cl.
CPC .............. *H05G 1/10* (2013.01); *A61B 6/42* (2013.01); *A61B 6/4208* (2013.01);
(Continued)

(58) Field of Classification Search
CPC ....... A61B 6/4283; A61B 6/44; A61B 6/4405; A61B 6/4411; A61B 6/4429;
(Continued)

(56) References Cited

U.S. PATENT DOCUMENTS 3,984,690 A 10/1976 Marshall, III
5,801,514 A 9/1998 Saeki
(Continued)

FOREIGN PATENT DOCUMENTS

CN 103220977 A 7/2013
CN 104184498 A 12/2014
(Continued)

OTHER PUBLICATIONS

An English translation of CN105762895 by Patent Translate dated Feb. 3, 2020.*
(Continued)

*Primary Examiner* — Allen C. Ho
(74) *Attorney, Agent, or Firm* — Sughrue Mion, PLLC

(57) ABSTRACT

Provided is a mobile X-ray apparatus including: an X-ray radiator configured to emit X-rays; a battery configured to supply power to the X-ray radiator; a charger configured to charge the battery; a battery management system (BMS) configured to receive power from the battery or the charger and output a first signal based on a state of the battery; and a first switch configured to be turned off according to the first signal to prevent power from being supplied to the BMS, wherein the first switch is further configured to be turned on by power supplied from the charger when the BMS is shut down.

4 Claims, 11 Drawing Sheets

(51) Int. Cl.
  *H05G 1/12* (2006.01)
  *H05G 1/26* (2006.01)
  *H05G 1/30* (2006.01)
  *H05G 1/32* (2006.01)
  *H05G 1/34* (2006.01)
  *H05G 1/36* (2006.01)
  *H05G 1/38* (2006.01)
  *H05G 1/54* (2006.01)
  *H05G 1/56* (2006.01)
  *A61B 6/00* (2006.01)

(52) U.S. Cl.
  CPC .......... *A61B 6/4233* (2013.01); *A61B 6/4283* (2013.01); *A61B 6/44* (2013.01); *A61B 6/4405* (2013.01); *A61B 6/4411* (2013.01); *A61B 6/4429* (2013.01); *A61B 6/4435* (2013.01); *A61B 6/4452* (2013.01); *A61B 6/56* (2013.01); *H05G 1/08* (2013.01); *H05G 1/12* (2013.01); *H05G 1/26* (2013.01); *H05G 1/265* (2013.01); *H05G 1/30* (2013.01); *H05G 1/32* (2013.01); *H05G 1/34* (2013.01); *H05G 1/36* (2013.01); *H05G 1/38* (2013.01); *H05G 1/54* (2013.01); *H05G 1/56* (2013.01)

(58) Field of Classification Search
  CPC ...... A61B 6/4435; A61B 6/4452; H05G 1/08; H05G 1/10; H05G 1/12; H05G 1/26; H05G 1/265; H05G 1/30; H05G 1/32; H05G 1/34; H05G 1/36; H05G 1/38; H05G 1/54; H05G 1/56
  USPC .......... 378/91, 101, 102, 108–112, 117, 118
  See application file for complete search history.

(56) References Cited

U.S. PATENT DOCUMENTS

| | | | |
|---|---|---|---|
| 5,825,155 A | 10/1998 | Ito | |
| 5,874,823 A | 2/1999 | Suzuki | |
| 5,892,351 A | 4/1999 | Faulk | |
| 5,945,807 A | 8/1999 | Faulk | |
| 5,990,577 A | 11/1999 | Kamioka | |
| 6,008,627 A | 12/1999 | Narita | |
| 6,064,185 A | 5/2000 | Ohno | |
| 6,094,034 A | 7/2000 | Matsuura | |
| 6,169,782 B1 | 1/2001 | Zetterlund | |
| 6,188,199 B1 | 2/2001 | Beutler | |
| 6,329,796 B1 | 12/2001 | Popescu | |
| 6,414,403 B2 | 7/2002 | Kitagawa | |
| 6,504,270 B1 | 1/2003 | Matsushita | |
| 6,661,200 B2 | 12/2003 | Odaohhara | |
| 7,024,574 B2 | 4/2006 | Odaohhara | |
| 7,057,309 B2 | 6/2006 | Odaohhara | |
| 7,183,748 B1 | 2/2007 | Unno | |
| 7,261,465 B2 | 8/2007 | Butzine | |
| 7,276,881 B2 | 10/2007 | Okumura et al. | |
| 7,309,159 B2 * | 12/2007 | Watanabe | A61B 6/10 378/117 |
| 7,375,498 B2 | 5/2008 | Yamamoto | |
| 7,495,416 B2 | 2/2009 | Sato et al. | |
| 7,573,034 B2 | 8/2009 | Heath | |
| 7,598,701 B2 | 10/2009 | Odaohhara | |
| 7,664,228 B2 | 2/2010 | Yi | |
| 7,737,658 B2 | 6/2010 | Sennami | |
| 7,805,263 B2 | 9/2010 | Mack | |
| 7,807,977 B2 | 10/2010 | Xue et al. | |
| 7,852,985 B2 * | 12/2010 | Liu | G01T 1/175 250/370.08 |
| 7,974,381 B2 | 7/2011 | Anderton | |
| 7,977,913 B2 | 7/2011 | Tan | |
| 8,031,837 B2 | 10/2011 | Spahn | |
| 8,080,802 B2 | 12/2011 | Nishino | |
| 8,130,000 B2 | 3/2012 | Botker | |
| 8,218,726 B2 | 7/2012 | Bressel | |
| 8,253,378 B2 | 8/2012 | Lee | |
| 8,319,506 B2 | 11/2012 | Liu | |
| 8,324,585 B2 * | 12/2012 | McBroom | A61B 6/4233 250/370.09 |
| 8,362,745 B2 | 1/2013 | Tinaphong | |
| 8,547,064 B2 | 10/2013 | Cooper | |
| 8,547,066 B2 | 10/2013 | Bieler | |
| 8,552,595 B2 | 10/2013 | Bohori | |
| 8,552,689 B2 | 10/2013 | Wang | |
| 8,675,328 B2 | 3/2014 | Altemose | |
| 8,690,425 B2 | 4/2014 | Kopcienski | |
| 8,721,176 B2 | 5/2014 | McBroom | |
| 8,786,257 B2 * | 7/2014 | Eguchi | A61B 6/00 320/127 |
| 8,798,235 B2 | 8/2014 | Ohta | |
| 8,798,236 B2 | 8/2014 | Ohta | |
| 8,929,510 B2 | 1/2015 | Nishino | |
| 8,966,235 B2 | 2/2015 | Dicks | |
| 9,044,191 B2 | 6/2015 | Nishino | |
| 9,060,741 B2 | 6/2015 | Fuse | |
| 9,101,316 B2 * | 8/2015 | Liu | A61B 6/4233 |
| 9,101,319 B2 | 8/2015 | Kojima | |
| 9,131,592 B2 * | 9/2015 | Kojima | A61B 6/4405 |
| 9,168,016 B2 | 10/2015 | Ohta | |
| 9,186,117 B2 | 11/2015 | Ogura | |
| 9,231,280 B2 | 1/2016 | Komatsu | |
| 9,265,476 B2 | 2/2016 | Iwakiri | |
| 9,277,298 B2 | 3/2016 | Yang et al. | |
| 9,322,934 B2 | 4/2016 | Ogura | |
| 9,337,901 B2 | 5/2016 | Takahashi | |
| 9,374,879 B2 | 6/2016 | Kuroki | |
| 9,380,988 B2 | 7/2016 | Kitano | |
| 9,425,631 B2 | 8/2016 | Furtner | |
| 9,456,799 B2 * | 10/2016 | Chicchetti | A61B 6/563 |
| 9,490,663 B1 | 11/2016 | Kim | |
| 9,521,983 B2 | 12/2016 | Jang | |
| 9,524,018 B2 | 12/2016 | Sultenfuss | |
| 9,554,768 B2 | 1/2017 | Kim | |
| 9,619,000 B2 | 4/2017 | Itabashi | |
| 9,655,582 B2 | 5/2017 | Shirota | |
| 9,697,725 B2 | 7/2017 | Oh | |
| 9,700,271 B2 | 7/2017 | Horiuchi | |
| 9,774,206 B2 | 9/2017 | Kim | |
| 9,778,380 B2 | 10/2017 | Enomoto | |
| 9,980,358 B2 * | 5/2018 | Kim | H05G 1/54 |
| 9,992,853 B2 * | 6/2018 | Kim | A61B 6/56 |
| 10,003,214 B2 * | 6/2018 | Nasiri | H02J 7/0014 |
| 10,028,710 B2 * | 7/2018 | Kim | A61B 6/105 |
| 10,051,718 B2 * | 8/2018 | Kim | A61B 6/4405 |
| 10,105,114 B2 * | 10/2018 | Shimizukawa | A61B 6/4283 |
| 10,278,668 B2 * | 5/2019 | Hishikawa | A61B 6/4405 |
| 10,321,883 B2 * | 6/2019 | Kim | H05G 1/12 |
| 2009/0128159 A1 | 5/2009 | Nakatsuji | |
| 2009/0207973 A1 | 8/2009 | Yi | |
| 2011/0042574 A1 | 2/2011 | Nishino et al. | |
| 2011/0140673 A1 | 6/2011 | Zhang | |
| 2013/0230142 A1 | 9/2013 | Murata | |
| 2014/0347057 A1 | 11/2014 | Oh et al. | |
| 2015/0245456 A1 | 8/2015 | Nishino | |
| 2016/0007432 A1 | 1/2016 | Ohta | |
| 2016/0064776 A1 | 3/2016 | Ro | |
| 2017/0027537 A1 | 2/2017 | Zhang et al. | |
| 2017/0086776 A1 | 3/2017 | Kim | |
| 2017/0374728 A1 | 12/2017 | Kuranisi | |
| 2018/0000443 A1 | 1/2018 | Matsuura | |
| 2018/0014396 A1 | 1/2018 | Imamura | |
| 2018/0035524 A1 | 2/2018 | Matsuura | |

FOREIGN PATENT DOCUMENTS

| | | |
|---|---|---|
| CN | 204761048 U | 11/2015 |
| CN | 105703439 A | 6/2016 |
| CN | 105762895 A | 7/2016 |
| EP | 2372380 A2 | 10/2011 |
| JP | 201295715 A | 5/2012 |
| KR | 100688135 B1 | 3/2007 |

(56) References Cited

FOREIGN PATENT DOCUMENTS

| KR | 10-2013-0031203 A | 3/2013 |
| KR | 10-2015-0047749 A | 5/2015 |
| KR | 10-2016-0024603 A | 3/2016 |

OTHER PUBLICATIONS

Communication dated Aug. 14, 2017, from the European Patent Office in counterpart European Application No. 17150836.9.
Communication dated Aug. 18, 2017, issued by the Korean Intellectual Property Office in corresponding Korean Application No. 10-2016-0181361.
Communication dated Sep. 20, 2019 by the State Intellectual Property Office of P.R. China in counterpart Chinese Application No. 201710156488.0.

* cited by examiner

MOBILE X-RAY APPARATUS INCLUDING A BATTERY MANAGEMENT SYSTEM

CROSS-REFERENCE TO RELATED APPLICATIONS

This application is a continuation of U.S. patent application Ser. No. 15/391,957, filed on Dec. 28, 2016 (now U.S. Pat. No. 9,992,853), which claims the benefit of Korean Patent Application No. 10-2016-0099134, filed on Aug. 3, 2016, and Korean Patent Application No. 10-2016-0181361, filed on Dec. 28, 2016 in the Korean Intellectual Property Office, the disclosures of which are incorporated herein in their entirety by reference.

BACKGROUND

1. Field

The present disclosure relates to mobile X-ray apparatuses including lithium ion batteries.

2. Description of the Related Art

X-rays are electromagnetic waves having wavelengths of 0.01 to 100 angstroms (Å), and are widely used, due to their ability to penetrate objects, in medical apparatuses for imaging the inside of a living body or in non-destructive testing equipment for industrial use.

An X-ray apparatus using X-rays may obtain X-ray images of an object by transmitting X-rays emitted from an X-ray source through an object and detecting a difference in intensities of the transmitted X-rays via an X-ray detector. The X-ray images may be used to examine an internal structure of an object and diagnose a disease of the object. The X-ray apparatus facilitates observation of an internal structure of an object by using a principle in which penetrating power of an X-ray varies depending on the density of the object and atomic numbers of atoms constituting the object. As a wavelength of an X-ray decreases, penetrating power of the X-ray increases and an image on a screen becomes brighter.

Since an X-ray radiator and an X-ray detector of the X-ray apparatus are generally affixed to a specific space, a patient needs to be transferred to an examination room where the X-ray apparatus is located for X-ray imaging.

However, a general X-ray apparatus has difficulty in performing X-ray imaging examinations on patients with mobility problems. Thus, a mobile X-ray apparatus has been developed to perform X-ray imaging without space limitations.

In the mobile X-ray apparatus, an X-ray radiator is mounted on a movable main body, and a portable X-ray detector is used. Due to this configuration, the mobile X-ray apparatus may be taken directly to a patient with reduced mobility in order to perform X-ray imaging.

SUMMARY

Provided are apparatuses for waking up a battery management system (BMS) that is shut down by supplying power to the battery management system (BMS).

Additional aspects will be set forth in part in the description which follows and, in part, will be apparent from the description, or may be learned by practice of the presented embodiments.

According to an aspect of an embodiment, a mobile X-ray apparatus includes: battery configured to supply power to an X-ray radiator; a charger configured to charge the battery; a battery management system (BMS) configured to determine a state of the battery by detecting at least one of a voltage and a temperature of the battery and output a first signal that is a shut down signal based on the determined state of the battery; a direct current DC-to-DC (DC-DC) converter configured to convert the power supplied by the battery into a driving power for driving the battery management system (BMS); and a first switch comprising a field effect transistor (FET) and configured to be turned off according to the first signal to prevent power from being supplied to the DC-DC converter, wherein the battery management system (BMS) is further configured to be shut down when the first switch is turned off, and the first switch is further configured to be turned on by power supplied from the charger when the battery management system (BMS) is shut down.

The mobile X-ray apparatus may further include a second switch configured to be turned on or off based on the first signal output from the battery management system (BMS), and the first switch is further configured to be turned on as the second switch is turned on.

The battery management system (BMS) is further configured to output a driving power for operating the second switch.

The second switch is further configured to be turned off when the battery management system (BMS) is shut down.

The battery management system (BMS) is further configured to output a third signal, and the first switch is further configured to be turned on by the third signal.

The mobile X-ray apparatus may further include a third switch configured to be turned on by the power supplied by the charger when the battery management system (BMS) is shut down.

The mobile X-ray apparatus may further include a fourth switch configured to remain in an on-state in the absence of a driving power and have one terminal connected to the third switch to control the third switch.

The battery management system (BMS) is further configured to output a driving power for operating the fourth switch.

The mobile X-ray apparatus may further include a discharge FET configured to be turned on or off based on a signal output from the battery management system (BMS) and to be turned on when the battery is discharged and be turned off when the battery is charged.

The discharge FET is further configured to, when turned off, form a current path from a minus terminal of the battery to the charger.

The mobile X-ray apparatus may further include a charge FET configured to be turned on or off based on a signal output from the battery management system (BMS) and to be turned on when the battery is charged and be turned off when the battery is discharged.

The charge FET is further configured to, when turned off, form a current path from the X-ray radiator to a minus terminal of the battery.

The battery may be a lithium ion battery.

According to another aspect of an embodiment, a mobile X-ray apparatus includes: an X-ray radiator configured to emit X-rays; a battery configured to supply power to the X-ray radiator; a battery management system (BMS) configured to be shut down based on a state of the battery; and a charger configured to supply power to the battery and the battery management system (BMS), wherein the battery management system (BMS) is further configured to be woken up by the power that is supplied from the charger when the battery management system (BMS) is shut down.

The mobile X-ray apparatus may further include a physical switch protruding outward therefrom, and the battery management system (BMS) may be woken up by the physical switch when the battery management system (BMS) is shut down.

According to an embodiment, the mobile X-ray apparatus may wake up the battery management system (BMS) that is shut down without using a separate switch by disconnecting an AC power cord provided on a main body from an outlet and then inserting the AC power cord into the outlet.

According to another embodiment, a wakeup switch may be provided on the main body of the mobile X-ray apparatus and be used to wake up the shutdown battery management system (BMS).

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
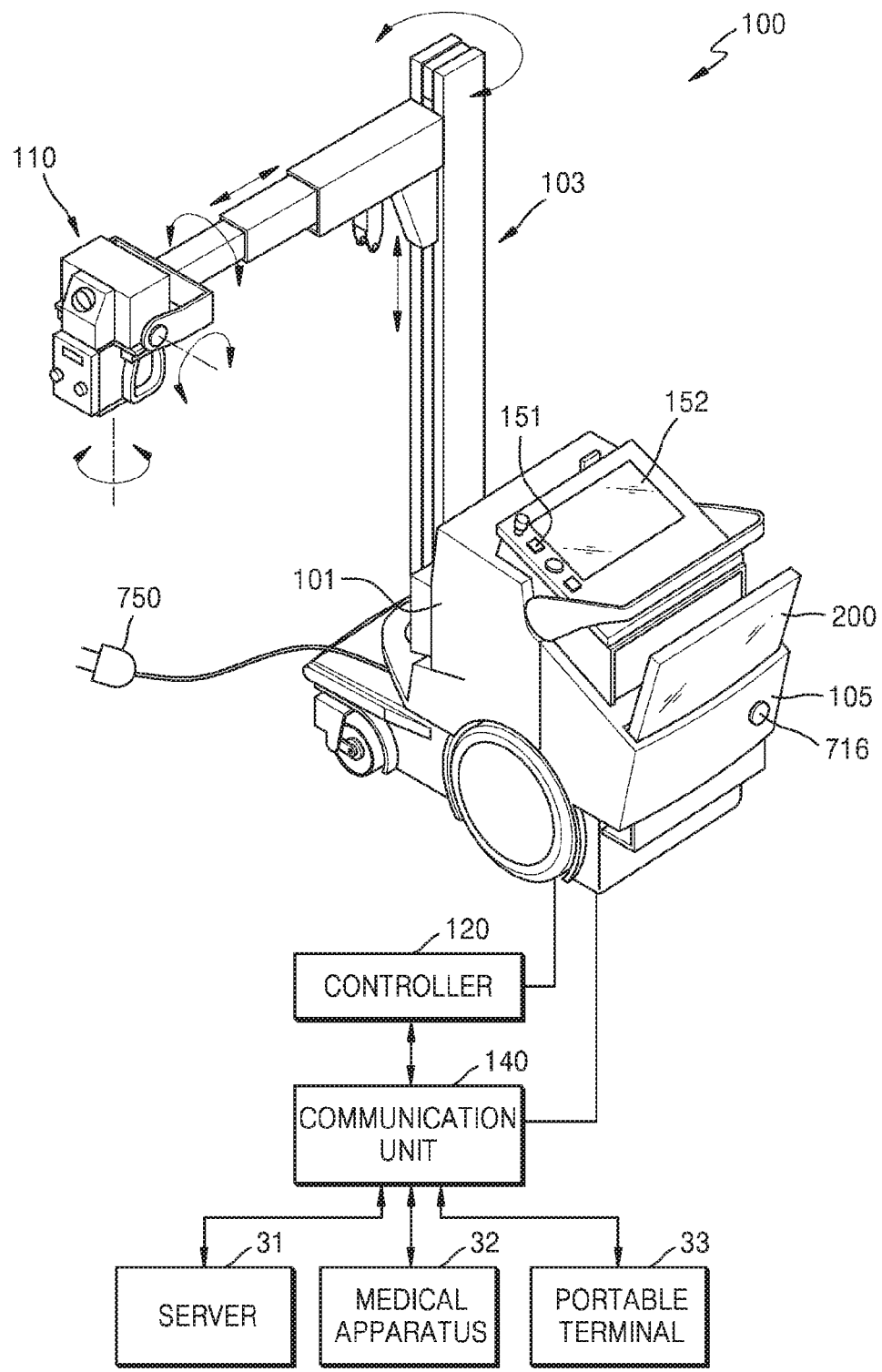
FIGS. 1A through 1C are external views and block diagrams of X-ray apparatuses implemented as mobile X-ray apparatuses, according to embodiments.

Various embodiments will be described more fully hereinafter with reference to the accompanying drawings. The embodiments and terms used herein are not intended to limit technologies described in the present disclosure to particular implementations, and the scope of the present disclosure should be construed as including all the changes, equivalents, and substitutions made to the embodiments. In the accompanying drawings, like reference numerals refer to like elements throughout.

Use of singular forms includes plural references as well unless expressly specified otherwise. As used herein, the expression such as "A or B" or "at least one of A and/or B" includes any and all combinations of one or more of the associated listed items. It will be understood that the terms "first", "second", etc. may be used herein to describe various elements or components regardless of the order or priority among the elements or components. The terms may only be used to distinguish one element or component from another element or component without limiting the elements or components. Expressions such as "at least one of," when preceding a list of elements, modify the entire list of elements and do not modify the individual elements of the list. Hereinafter, the operating principles and embodiments of the present disclosure will be described in detail with reference to the accompanying drawings.

Throughout the specification, it should be noted that when an element (e.g., a first element) is referred to as being "connected" or "coupled" (functionally or via a communication network) to another element (e.g., a second element), it can be connected or coupled to the other element directly or via another element (e.g., a third element).

In the present specification, the expression "configured (or set) to" may be interchangeably used with, for example, "suitable for," "having the capacity to," "adapted to," "made to," "capable of," or "designed to" in hardware or software, depending on the circumstances. In some cases, the expression "a device configured to" may mean that the device "is capable of" doing something together with other devices or components. For example, the phrase "a processor configured (or set) to perform operations A, B, and C" may mean a dedicated processor (e.g., embedded processor) for performing the corresponding operations or a general-purpose processor (e.g., a central processing unit (CPU) or an application processor (AP)) that can perform the corresponding operations by executing one or more software programs stored in a memory device.

Throughout the specification, a "user" may be a person who manipulates a mobile X-ray apparatus. Furthermore, the "user" may refer to a device (e.g., an artificial intelligence (AI) electronic device, a robot, or the like) for performing manipulation of the mobile X-ray apparatus.

The term 'part' or 'portion' used herein may be implemented using hardware or software, and according to embodiments, a plurality of 'parts' or 'portions' may be formed as a single unit or element, or one 'part' or 'portion' may include a plurality of units or elements.

In the present specification, an image may include a medical image obtained by a magnetic resonance imaging (MRI) apparatus, a computed tomography (CT) apparatus, an ultrasound imaging apparatus, an X-ray imaging apparatus, or another medical imaging apparatus.

Furthermore, in the present specification, an 'object' may be a target to be imaged and include a human, an animal, or a part of a human or animal. For example, the object may include a body part (an organ, etc.) or a phantom.

Hereinafter, the operating principles and embodiments of the present disclosure will be described in detail with reference to the accompanying drawings.

Figure 1B:
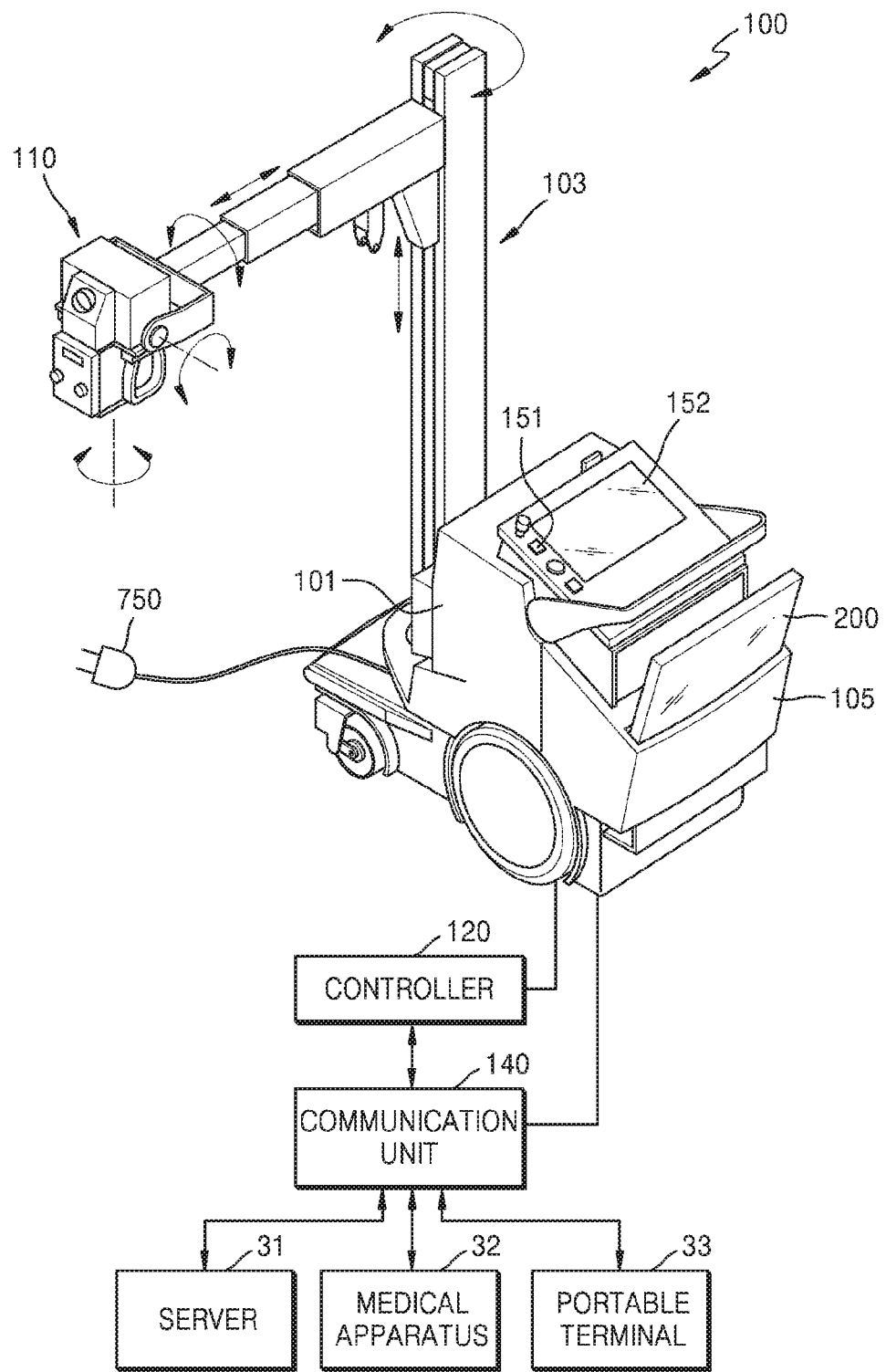
Figure 1C:
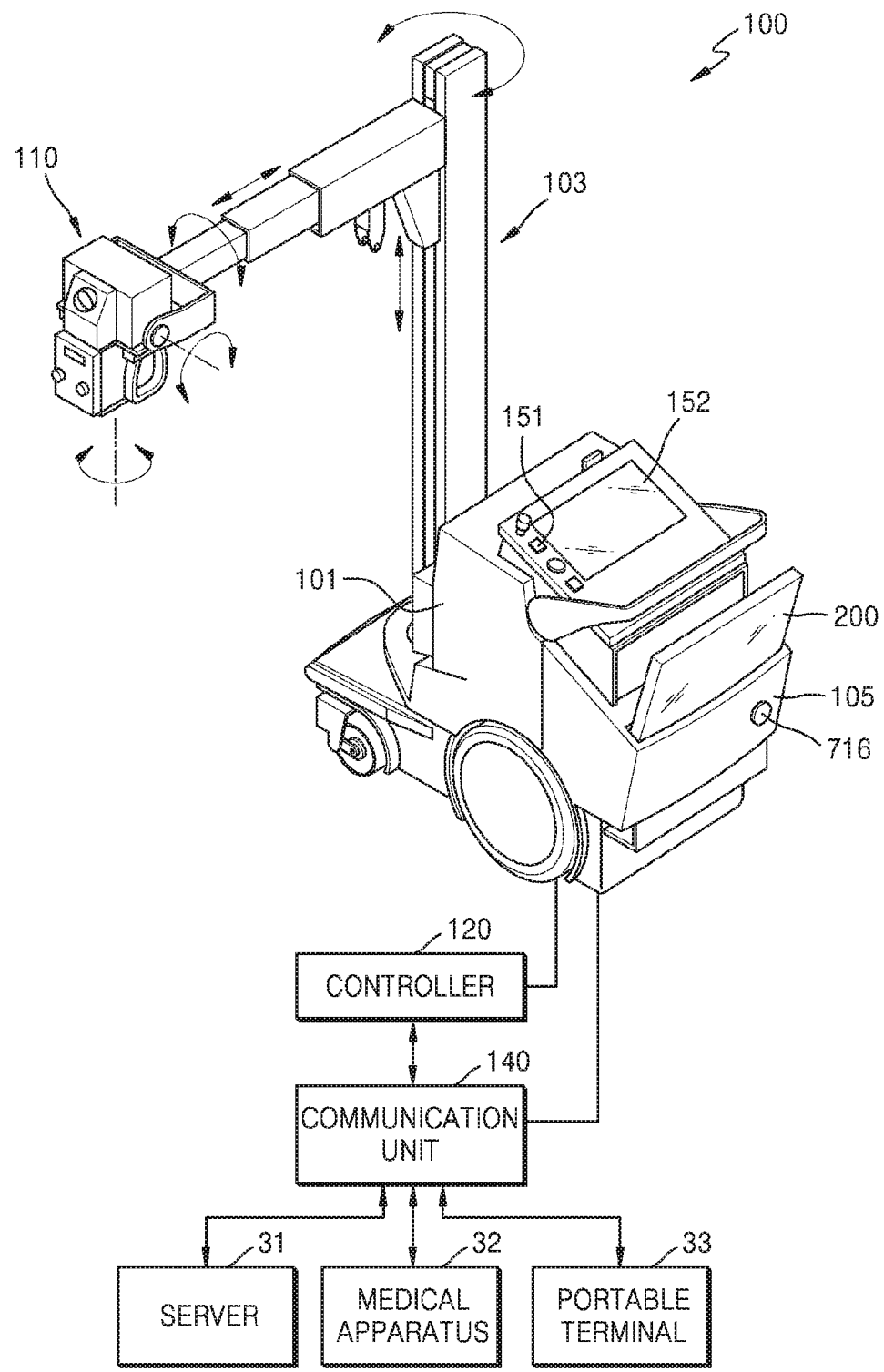

FIGS. 1A through 1C are external views and block diagrams of X-ray apparatuses 100 implemented as mobile X-ray apparatuses, according to embodiments.

Referring to FIG. 1A, the X-ray apparatus 100 according to the present embodiment includes an X-ray radiator 110 for generating and emitting X-rays, an input device 151 for receiving a command from a user, a display 152 for providing information to the user, a controller 120 for controlling the X-ray apparatus 100 according to the received command, and a communication unit 140 for communicating with an external device.

The X-ray radiator 110 may include an X-ray source for generating X-rays and a collimator for adjusting a region irradiated with the X-rays generated by the X-ray source.

When the X-ray apparatus 100 is implemented as a mobile X-ray apparatus, a main body 101 connected to the X-ray radiator 110 is freely movable, and an arm 103 connecting the X-ray radiator 110 and the main body 101 to each other is also rotatable and linearly movable. Thus, the X-ray radiator 110 may be moved freely in a three-dimensional (3D) space.

The input device 151 may receive commands for controlling imaging protocols, imaging conditions, imaging timing, and locations of the X-ray radiator 110. The input device 151 may include a keyboard, a mouse, a touch screen, a voice recognizer, etc.

The display 152 may display a screen for guiding a user's input, an X-ray image, a screen for displaying a state of and the like.

The controller 120 may control in the X-ray apparatus 100, aging conditions and imaging timing of the X-ray radiator 110 according to a control command input by the user and generate a medical image based on image data received from an X-ray detector 200. Furthermore, the controller 120 may control a position or orientation of the X-ray radiator 110 according to imaging protocols and a position of an object.

The controller 120 may include a memory configured to store programs for performing the above operations of the X-ray apparatus 100 as well as operations thereof that will be described below and a processor configured to execute the stored programs. The controller 120 may include a single processor or a plurality of processors. When the controller 120 includes the plurality of processors, the plurality of processors may be integrated onto a single chip or be physically separated from one another.

A holder 105 may be formed on the main body 101 so as to accommodate the X-ray detector 200. Furthermore, a charging terminal is disposed in the holder 105 so as to charge the X-ray detector 200. In other words, the holder 105 may be used not only to accommodate but also to charge the X-ray detector 200.

The input device 151, the display 152, the controller 120, and the communication unit 140 may be provided on the main body 101. Image data acquired by the X-ray detector 200 may be transmitted to the main body 101 for image processing, and then the resulting image may be displayed on the display 152 or transmitted to an external device via the communication unit 140.

Furthermore, the controller 120 and the communication unit 140 may be separate from the main body 101, or only some components of the controller 120 and the communication unit 140 may be provided on the main body 101.

The X-ray apparatus 100 may be connected to external devices such as an external server 31, a medical apparatus 32, and a portable terminal 33 (e.g., a smart phone, a tablet PC, or a wearable device) in order to transmit or receive data via the communication unit 140.

The communication unit 140 may include at least one component that enables communication with an external device. For example, the communication unit 140 may include at least one of a local area communication module, a wired communication module, and a wireless communication module Furthermore, the communication unit 140 may receive a control signal from an external device and transmit the received control signal to the controller 120 so that the controller 120 may control the X-ray apparatus 100 according to the received control signal.

Alternatively, by transmitting a control signal to an external device via the communication unit 140, the controller 120 may control the external device according to the transmitted control signal. For example, the external device may process data according to a control signal received from the controller 120 via the communication unit 140.

Furthermore, the communication unit 140 may further include an internal communication module that enables communications between components of the X-ray apparatus 100. A program for controlling the X-ray apparatus 100 may be installed on the external device and may include instructions for performing some or all of the operations of the controller 120.

The program may be preinstalled on the portable terminal 33, or a user of the portable terminal 33 may download the program from an external server 31 providing an application for installation. The external server 31 for providing an application may include a recording medium having the program recorded thereon.

In addition, the main body 101 may be equipped with an alternating current (AC) power cord 750 and/or a switch 716. The user may connect the AC power cord 750 to an outlet (not shown) when a battery management system (BMS) is shut down to wake up the battery management system (BMS) from shutdown. Furthermore, the user presses the switch 716 when the battery management system (BMS) is shut down to wake up the battery management system (BMS) from shutdown.

According to embodiments, the user may use one of the AC power cord 750 and the switch 716 in the main body 101 to wake up the battery management system (BMS) that is shut down.

Referring to FIG. 1B, a main body 101 includes an AC power cord 750 but is not equipped with the switch (716 of FIG. 1A). In this case, the user may wake up a battery management system (BMS) that is shut down by connecting the AC power cord 750 to an outlet (not shown).

Referring to 1C, a main body 101 is equipped with a switch 716. In this case, the user may press the switch 716 when a battery management system (BMS) is shut down to wake up the shutdown battery management system (BMS). The switch 716 may be positioned on outside of a holder 105 for accommodating an X-ray detector 200 or on a side of the main body 101.

Figure 2:
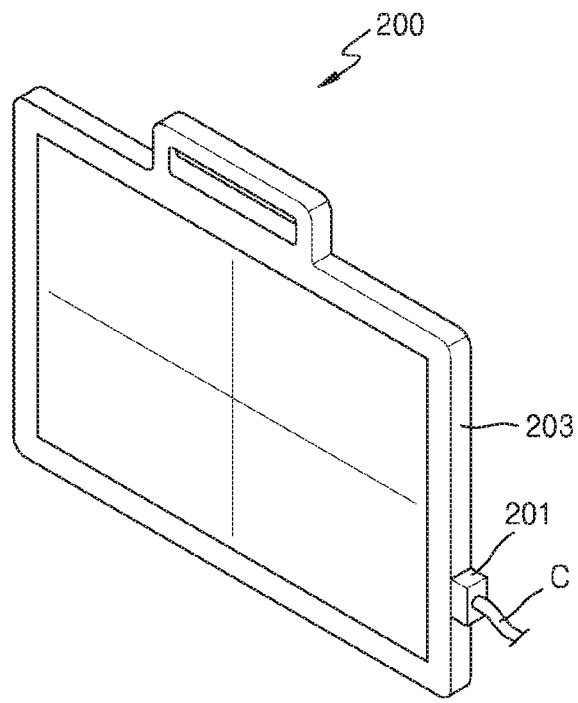
FIG. 2 is an external view of an X-ray detector included in each of the X-ray apparatuses of FIGS. 1A through 1C.

FIG. 2 is an external view of the X-ray detector 200.

As described above, the X-ray detector 200 used in the X-ray apparatus 100 may be implemented as a portable X-ray detector. In this case, the X-ray detector 200 may be equipped with a battery for supplying power to operate wirelessly, or as shown in FIG. 2, may operate by connecting a charge port 201 to a separate power supply via a cable C.

A case 203 maintains an external appearance of the X-ray detector 200 and has therein a plurality of detecting elements for detecting X-rays and converting the X-rays into image data, a memory for temporarily or permanently storing the image data, a communication module for receiving a control signal from the X-ray apparatus 100 or transmitting the image data to the X-ray apparatus 100, and a battery. Furthermore, image correction information and intrinsic identification (ID) information of the X-ray detector 200 may be stored in the memory, and the stored ID information may be transmitted together with the image data during communication with the X-ray apparatus 100.

Figure 3:
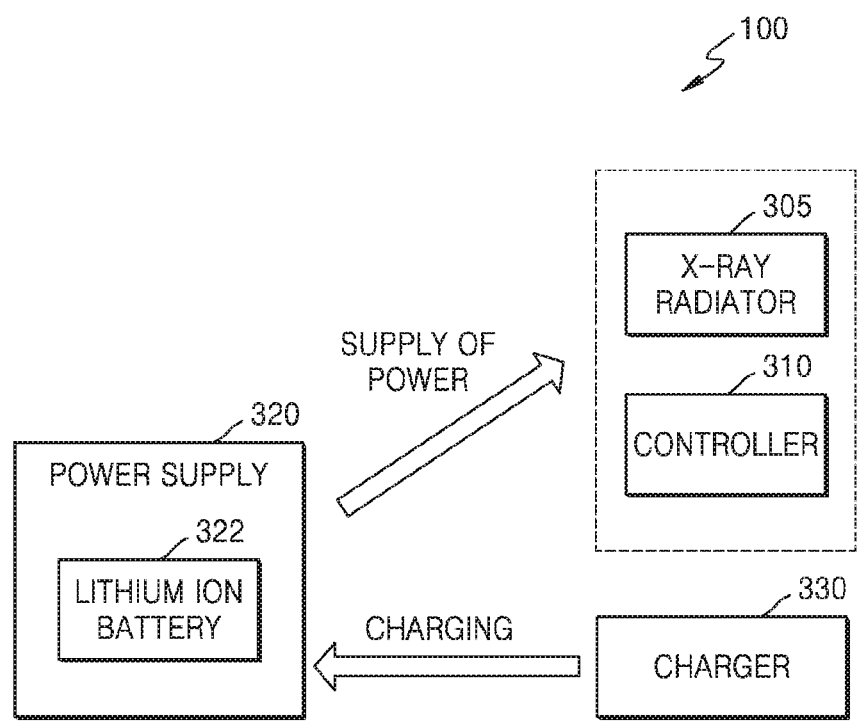
FIG. 3 is a block diagram of an X-ray apparatus according to an embodiment.

FIG. 3 is a block diagram of an X-ray apparatus 100 according to an embodiment.

Referring to FIG. 3, the X-ray apparatus 100 according to the present embodiment may include an X-ray radiator 305, a controller 310, a power supply 320 including a lithium ion battery 322, and a charger 330. The X-ray apparatus 100 may further include a high voltage generator (not shown) provided on a main body. The X-ray apparatus 100 of FIG. 3 may be implemented as a mobile X-ray apparatus as shown in FIG. 1A, and FIG. 3 illustrates only components related to the present embodiment. Thus, it will be understood by those of ordinary skill in the art that the X-ray apparatus 100 may further include common components other than those shown in FIG. 3.

The descriptions with respect to the X-ray radiator 110 in FIG. 1A may apply to descriptions with respect to the X-ray radiator 305, and thus, are not repeated. Furthermore, the descriptions with respect to the controller 120 in FIG. 1A may apply to descriptions with respect to the controller 310, and thus, are not repeated.

The power supply 320 may supply power to a load via the lithium ion battery 322. For example, the load may include the X-ray radiator 305, the controller 310, and various other components of the X-ray apparatus 100, to which power is supplied. In other words, the lithium ion battery 322 may supply operating power to the X-ray radiator 305 and the controller 310.

Furthermore, the power supply 320 may supply, via the lithium ion battery 322, operating power to components of the X-ray apparatus 100 that require the operating power. For example, the power supply 320 may supply operating power to the input device 151, the display 152, and the communication unit 140 of the X-ray apparatus 100 via the lithium ion battery 322.

The power supply 320 may control overcurrent that occurs during emission of X-rays by the X-ray radiator 305. In other words, as the X-ray radiator 305 emits X-rays, overcurrent that is higher than a normal operating current may flow in the power supply 320, and the power supply 320 may control the overcurrent. According to an embodiment, in order to control overcurrent, the power supply 320 may construct a circuit consisting of a discharge field effect transistor (FET) having FETs connected in parallel and a charge FET. According to another embodiment, in order to control the overcurrent, the power supply 320 may construct a circuit including current sensors having different capacities for measuring the amount of discharge current.

The charger 330 may charge the power supply 320. In detail, the charger 330 may supply a charging power to charge the lithium ion battery 322 of the power supply 320. In this case, the charging power may be a power generated by the charger 330. According to an embodiment, the charger 330 may be combined with an external power supply to receive power from the external power supply. The charger 330 may then control the received power according to a user input or arithmetic operations performed within the X-ray apparatus 100, to supply a charging power to the lithium ion battery 322.

The power supply 320, the charger 330, and the controller 310 may each include a communication interface that enables communication therebetween. For example, the power supply 320, the charger 330, and the controller 310 may communicate with one another via their communication interfaces according to a controller area network (CAN) protocol. Furthermore, according to another embodiment, communications may be performed among the power supply 320, the charger 330, and the controller 310 by using a high-speed digital interface such as low voltage differential signaling (LVDS), an asynchronous serial communication protocol such as a universal asynchronous receiver transmitter (UART), a low-latency network protocol such as an error synchronous serial communication protocol, or other various communication methods that are obvious to those of ordinary skill in the art. Furthermore, the power supply 320, the charger 330, and the controller 310 may each be constituted by a different module. Thus, since the controller 310 does not need to directly monitor a high voltage, a high voltage circuit is not needed within the controller 310. This may consequently reduce the risks associated with the high voltage circuit, thereby effectively improving stability.

In detail, in a mobile X-ray apparatus using a conventional lead-acid battery, a controller 310 may include a circuit for monitoring a high voltage state, and may be damaged by high voltages. On the other hand, in the X-ray apparatus 100 according to the present embodiment, a battery management system (BMS) of the power supply 320 may monitor a high voltage state and transmit the high voltage state to the controller 310. This configuration may reduce the risk of damage to the controller 310.

Furthermore, when the power supply 320, the charger 330, and the controller 310 are each composed of a different module, they may be used for different mobile X-ray apparatuses and thus share a common platform. Furthermore, by applying a shield case to each of the power supply 320, the charger 330, and the controller 310, it is possible to suppress Electro Magnetic Interference (EMI)/Electro Magnetic Compatibility (EMC) noise that may occur therebetween.

Figure 4:
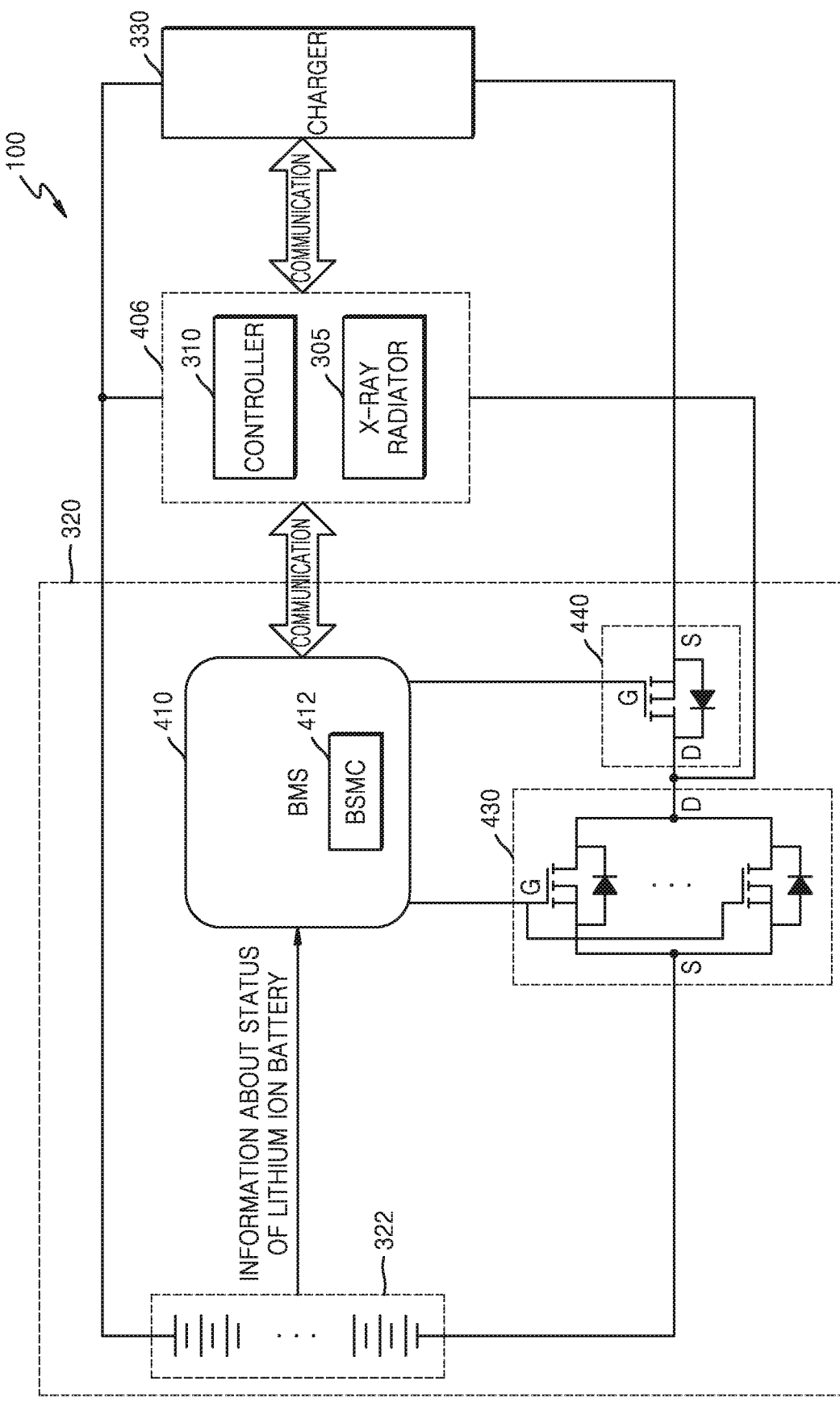
FIG. 4 illustrates components of a power supply included in a mobile X-ray apparatus, according to an embodiment.

FIG. 4 illustrates components of a power supply 320 included in a mobile X-ray apparatus 100, according to an embodiment.

Referring to FIG. 4, the power supply 320 may include a lithium ion battery 322, a battery management system (BMS) 410, a discharge FET 430, and a charge FET 440. The power supply 320 shown in FIG. 4 includes only components related to the present embodiment. Furthermore, the power supply 320 may include a voltage sensor (not shown) for detecting a voltage and a temperature sensor (not shown) for detecting a temperature. Thus, one of ordinary skill in the art will understand that the power supply 320 may further include common components other than those shown in FIG. 4.

The lithium ion battery 322 is a type of secondary battery and consists of three components: an anode, a cathode, and an electrolyte. For example, lithium cobalt oxide ($LiCoO_2$) or lithium iron phosphate ($LiFePO_4$) may be used for the anode, and graphite may be used for the cathode. The lithium ion battery 322 may include a combination of a plurality of battery cells connected to each other. For example, the lithium ion battery 322 may include a total of three hundred and fifty-two (352) cells, i.e., a serial connection of 88 cells and a parallel connection of 4 cells.

Furthermore, the lithium ion battery 322 may be suitable for use in a mobile X-ray apparatus 100 due to its smaller size and lighter weight than conventional lead-acid batteries. For example, since a total mass of the power supply 320 including the lithium ion battery 322 and a peripheral circuit may be 33.2 kg, the total mass may be less than 35 kg, which is the maximum allowable gross mass for carrying on an aircraft. Thus, the power supply 320 may be transported by air as a single component.

The mobile X-ray apparatus 100 may supply power to an X-ray radiator 305 through a battery, and may include the battery management system (BMS) 410 configured to operate a protection circuit by checking a voltage and a temperature of the battery.

The battery management system (BMS) 410 may detect a state of the lithium ion battery 322, such as a voltage and a temperature thereof. According to an embodiment, the battery management system (BMS) 410 may include a battery stack monitor circuit 412 designed to monitor a voltage of the lithium ion battery 322 and a temperature of a battery cell. The battery management system (BMS) 410 may control and manage the power supply 320 based on the state of the lithium ion battery 322. Furthermore, the battery management system (BMS) 410 may control on/off states of the charge FET 440 and the discharge FET 430 to manage a charge path and a discharge path, respectively.

Furthermore, the battery management system (BMS) 410 may operate a protection circuit based on the state of the lithium ion battery 322. In other words, the battery management system (BMS) 410 may operate, based on the state of the lithium ion battery 322, the protection circuit to protect the lithium ion battery 322 from dangerous conditions. In detail, based on the state of the lithium ion battery 322, the battery management system (BMS) 410 may operate the protection circuit to protect the lithium ion battery 322 against at least one of over-discharge, overcurrent, overheating, and unbalancing between battery cells.

The battery management system (BMS) 410 may operate, based on the state of the lithium ion battery 322, the protection circuit by checking states of over-discharge, overcurrent, overheating, and unbalancing between battery cells, and may accordingly be shut down.

The battery management system (BMS) 410 may operate the protection circuit when the lithium ion battery 322 is in an over-discharged state where a voltage of the lithium ion battery 322 is lower than a reference voltage. For example, if a voltage of the lithium ion battery 322 drops to less than or equal to 275 V, the battery management system (BMS) 410 may operate a shutdown circuit to turn itself off. Furthermore, the battery management system (BMS) 410 may operate the protection circuit when the lithium ion battery 322 is in an overcurrent state where a current of the lithium ion battery 322 is higher than a reference value. For example, if the current of the lithium ion battery 322 is greater than or equal to 40 A, the battery management system (BMS) 410 may operate a shutdown circuit to reset itself. The battery management system (BMS) 410 may also operate the protection circuit when the lithium ion battery 322 is in an overheated state where a temperature of the lithium ion battery 322 is higher than a reference value. For example, if the temperature of the lithium ion battery 322 is greater than or equal to 70° C., the battery management system (BMS) 410 may operate the protection circuit to shut off a charge path and a discharge path. Furthermore, when the lithium ion battery 322 is unbalanced between cells, the battery management system (BMS) 410 may operate the protection circuit. For example, if a voltage difference between cells in the lithium ion battery 322 remains greater than or equal to 0.5 V for ten (10) seconds or more, the battery management system (BMS) 410 may operate a shutdown circuit to turn itself off.

The battery management system (BMS) 410 may communicate with a controller 310 via a communication interface to monitor a state of the power supply 320.

A load 406 may receive power via a charge path and/or a discharge path.

The discharge FET 430 may include a plurality of FETs connected in parallel. Since overcurrent may flow in the power supply 320 during X-ray emission by the X-ray radiator 305, the FETs having a specific capacity in the discharge FET 430 may be connected in parallel. In other words, by connecting the FETs having the specific capacity in parallel, a maximum allowable current capacity of the discharge FET 430 may be increased. For example, if overcurrent greater than or equal to 300 A flows within the power supply 320 during X-ray emission by the X-ray radiator 305, the discharge FET 430 may be constituted by four (4) parallel connected FETs having a capacity of 100 A for protection against the overcurrent.

According to an embodiment, the discharge FET 430 and the charge FET 440 may each be constituted by an N-channel FET.

The discharge FET 430 and the charge FET 440 may control a path of discharge or charge current when the lithium ion battery 322 is discharged or charged. According to an embodiment, when the lithium ion battery 322 is discharged, the charge FET 440 may be turned off, and a discharge current loop may be formed by the discharge FET 430. According to another embodiment, when the lithium ion battery 322 is charged, the discharge FET 430 may be turned off, and a charge current loop may be formed by a body diode of the discharge FET 430 and the charge FET 440. Furthermore, the lithium ion battery 322 may be discharged and charged at the same time via the discharge FET 430 and the charge FET 440.

Furthermore, while FIG. 4 shows that a load 406 for receiving a power from the lithium ion battery 322 includes the controller 310 and the X-ray radiator 305, the load 406 may further include other components of the X-ray apparatus 100 that require power.

Figure 5:
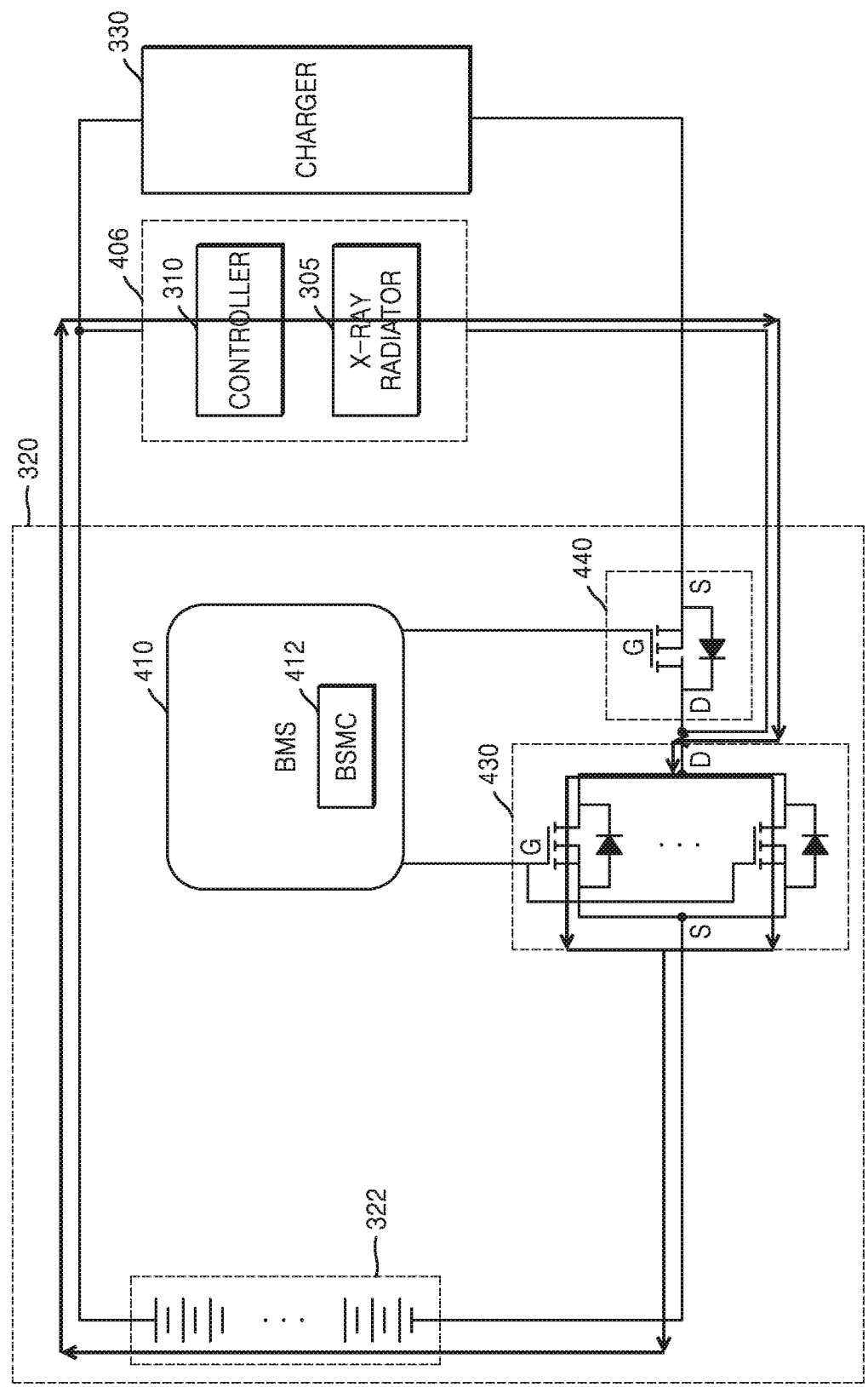
FIG. 5 is a schematic diagram illustrating discharging of a lithium ion battery according to an embodiment.

FIG. 5 is a schematic diagram illustrating discharging of a lithium ion battery 322 according to an embodiment.

An on/off state of a discharge FET 430 may be controlled based on a signal output from a battery management system (BMS) 410. In detail, the discharge FET 430 may be turned on when the lithium ion battery 322 is discharged and be turned off when the lithium ion battery 322 is charged. The signal may be coupled to a gate terminal of the discharge FET 430. When the discharge FET 430 is turned off, a current path is formed from a minus terminal of the lithium ion battery 322 to a charger 330 via a body diode.

In detail, when the lithium ion battery 322 is discharged, a charge FET 440 may be turned off since a source (S) voltage of the charge FET 440 is higher than a drain (D) voltage thereof. Furthermore, when the lithium ion battery 322 is discharged, a discharge FET 430 may be turned on since a drain (D) voltage of the discharge FET 430 is higher than a source (S) voltage thereof.

Thus, as shown in FIG. 5, a discharge current loop may be formed in a clockwise direction in which a discharge current flows through a load 406, the discharge FET 430, and the lithium ion battery 322. Furthermore, even when the charge FET 440 is turned off, discharging of the lithium ion battery 322 may be performed normally.

Figure 6:
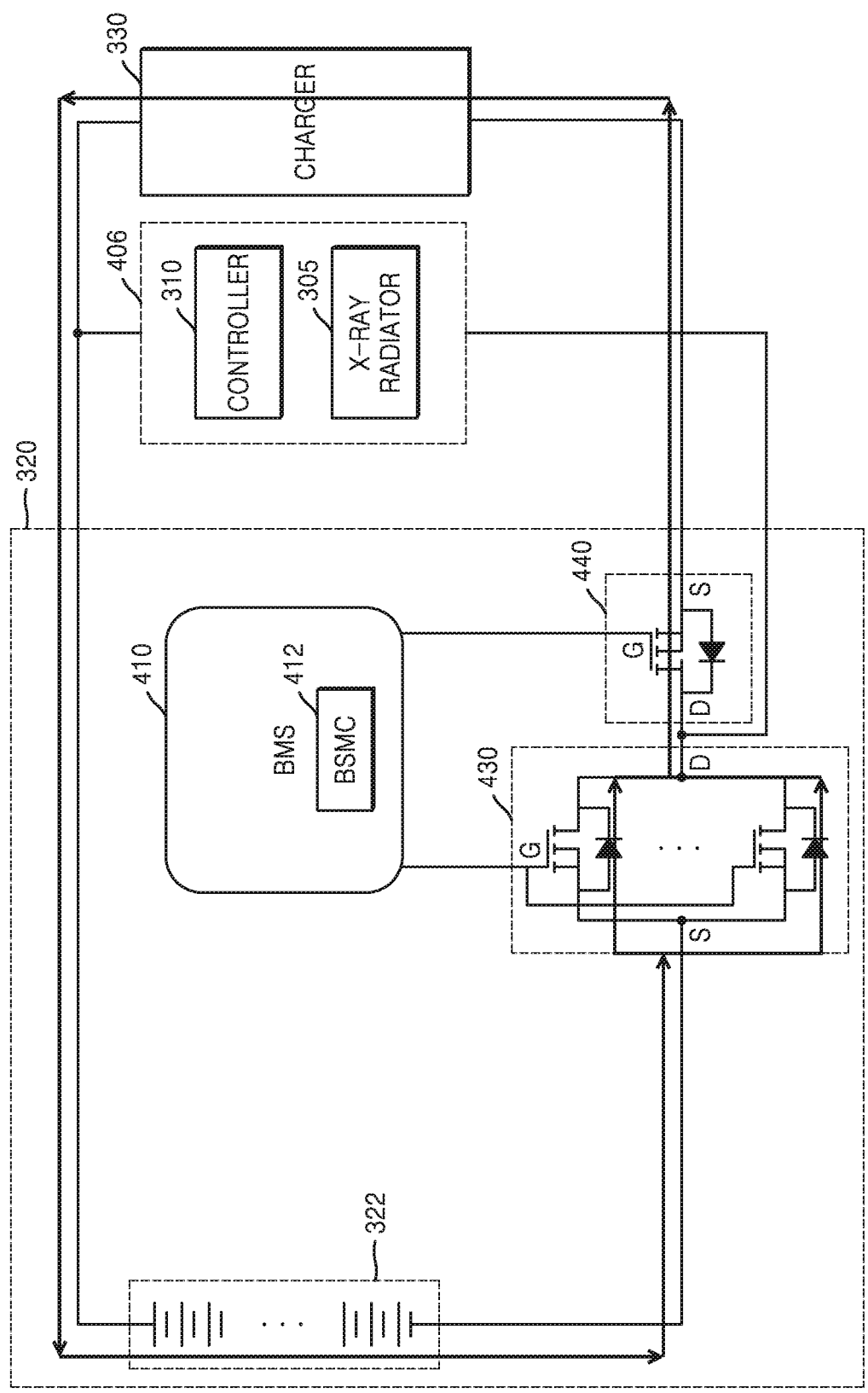
FIG. 6 is a schematic diagram illustrating charging of a lithium ion battery according to an embodiment.

FIG. 6 is a schematic diagram illustrating charging of a lithium ion battery 322 according to an embodiment.

An on/off state of a charge FET 440 may be controlled based on a signal output from a battery management system (BMS) 410. In detail, the charge FET 440 may be turned on when the lithium ion battery 322 is charged and be turned off when the lithium ion battery 322 is discharged. When the charge FET 440 is turned off, a current path from the load 406 to a minus terminal of the lithium ion battery 322 may be formed.

In detail, when the lithium ion battery 322 is charged, a discharge FET 430 may be turned off since a source (S) voltage of the discharge FET 430 is higher than a drain (D) voltage thereof. When the discharge FET 430 is turned off, a charge current may flow through a body diode of the discharge FET 430. Furthermore, when the lithium ion battery 322 is charged, the charge FET 440 may be turned on since a drain (D) voltage of the charge FET 440 is higher than a source (S) voltage thereof.

Thus, as shown in FIG. 6, a charge current loop may be formed in a counter-clockwise direction in which a charge current flows through a charger 330, the lithium ion battery 322, the body diode of the discharge FET 430, and the charge FET 440. Furthermore, even when the discharge FET 430 is turned off, charging of the lithium ion battery 322 may be performed normally.

Figure 7:
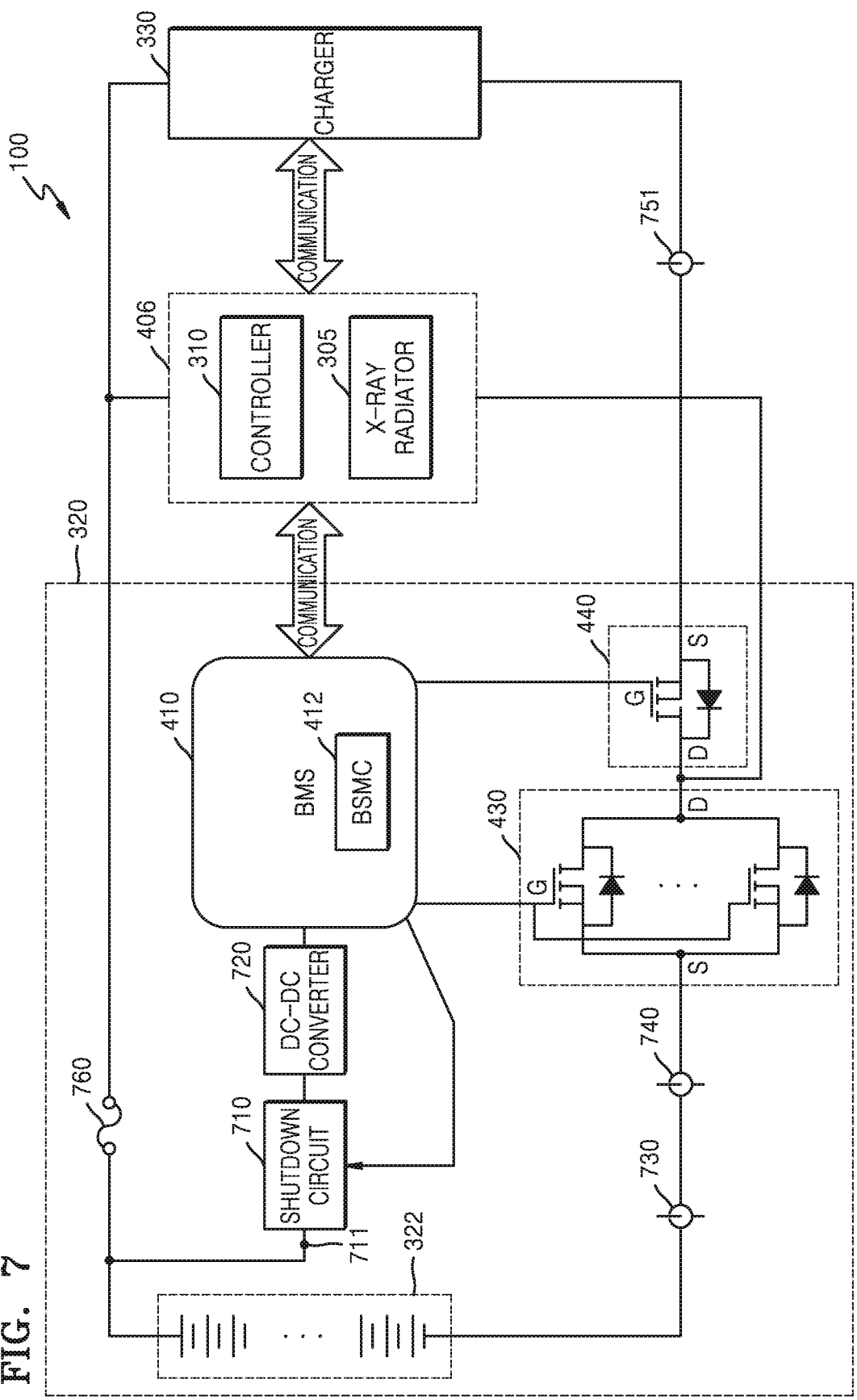
FIG. 7 is a detailed block diagram of a mobile X-ray apparatus according to an embodiment.

FIG. 7 is a detailed block diagram of a mobile X-ray apparatus 100 according to an embodiment.

Referring to FIG. 7, a power supply 320 may include a lithium ion battery 322, a battery management system (BMS) 410, a discharge FET 430, a charge FET 440, a shutdown circuit 710, a first current sensor 730, a second current sensor 740, a DC-to-DC (DC-DC) converter 720, and a fuse 760. Furthermore, the X-ray apparatus 100 may include a third current sensor 751. Since the lithium ion battery 322, the battery management system (BMS) 410, the discharge FET 430, and the charge FET 440 respectively correspond to the lithium ion battery 322, the battery management system (BMS) 410, the discharge FET 430, and the charge FET 440 described with reference to FIG. 4, detailed descriptions thereof will be omitted below. The first and second current sensors 730 and 740 may include a Hall sensor, and the shutdown circuit 710 that is a protection circuit may include a switching circuit such as a FET.

The battery management system (BMS) 410 may detect current of the lithium ion battery 322 by using different current sensors, i.e., the first and second current sensors 730 and 740. In detail, the battery management system (BMS) 410 may detect current flowing in the lithium ion battery 322 by using the first current sensor 730. The first current sensor 730 may be a small-capacity sensor for detecting a current having a relatively low intensity. In other words, the first current sensor 730 may be a sensor for detecting a current having an intensity less than or equal to a reference level. For example, the first current sensor 730 may detect a current that is less than or equal to 50 A. Furthermore, when overcurrent flows in the lithium ion battery 322, the battery management system (BMS) 410 may detect overcurrent flowing in the lithium ion battery 322 by using the second current sensor 740. The second current sensor 740 may be a large-capacity sensor for detecting a current having a relatively high intensity. In other words, the second current sensor 740 may be a sensor for detecting a current having an intensity greater than or equal to a reference level. For example, the second current sensor 740 may detect a current that is greater than or equal to 300 A.

According to an embodiment, the battery management system (BMS) 410 may detect, via the first current sensor 730, current flowing in the lithium ion battery 322 by activating the first current sensor 730 while deactivating the second current sensor 740. Then, when an X-ray radiator 305 emits X-rays, the battery management system (BMS) 410 may detect overcurrent that occurs during the X-ray emission via the second current sensor 740 by activating the second current sensor 740 while deactivating the first current sensor 730. Subsequently, when the X-ray emission is completed, the battery management system (BMS) 410 may detect, via the first current sensor 730, current flowing in the lithium ion battery 322 by activating the first current sensor 730 while deactivating the second current sensor 740. According to an embodiment, the battery management system (BMS) 410 may receive an X-ray emission preparation signal from a controller 310 and activate the second current sensor 740 to detect overcurrent occurring during X-ray emission via the second current sensor 740.

The battery management system (BMS) 410 may check the residual amount of the lithium ion battery 322 based on the amount of current detected using the first and second current sensors 730 and 740. In detail, the battery management system (BMS) 410 may use Coulomb Counting Based Gauging to check the residual amount of the lithium ion battery 322 based on the detected amount of current.

Furthermore, the mobile X-ray apparatus 100 may further include the third current sensor 751 for measuring a charge current. In other words, the mobile X-ray apparatus 100 may further include the third current sensor 751 at an output terminal of the charger 330. When the lithium ion battery 322 is charged and discharged at the same time, current measured by the first or second current sensor 730 or 740 may be a sum of a discharge current and a charge current. Thus, in order to accurately measure a discharge current and a charge current, the mobile X-ray apparatus 100 may measure the charge current by using the third current sensor 751.

The battery management system (BMS) 410 may receive signals indicating that the X-ray radiator 305 starts emission of X-rays and that the X-ray radiator 305 completes the emission of X-rays from the controller 310 via a communication interface.

The battery management system (BMS) 410 may output a first signal based on a state of the lithium ion battery 322. The first signal may be a shut down signal that is applied to the shutdown circuit 710. The battery management system (BMS) 410 may turn itself off by using the shutdown circuit 710. When the battery management system (BMS) 410 checks a state of the lithium ion battery 322 to detect hazardous conditions such as over-discharge and over-charge, the battery management system (BMS) 410 may turn itself off by using the shutdown circuit 710 that serves as a protection circuit. When the battery management system (BMS) 410 turns itself off, power being supplied to the controller 310 is also cut off, so that the controller 310 may also turn off.

The fuse 760 is designed to stop continuous flowing of excessive current that is greater than a nominal value in the power supply 320 and may protect a battery cell when the lithium ion battery 322 is subjected to an external short circuit.

The DC-DC converter 720 may convert power supplied by the lithium ion battery 322 into a DC power for driving the battery management system (BMS) 410.

Figure 8:
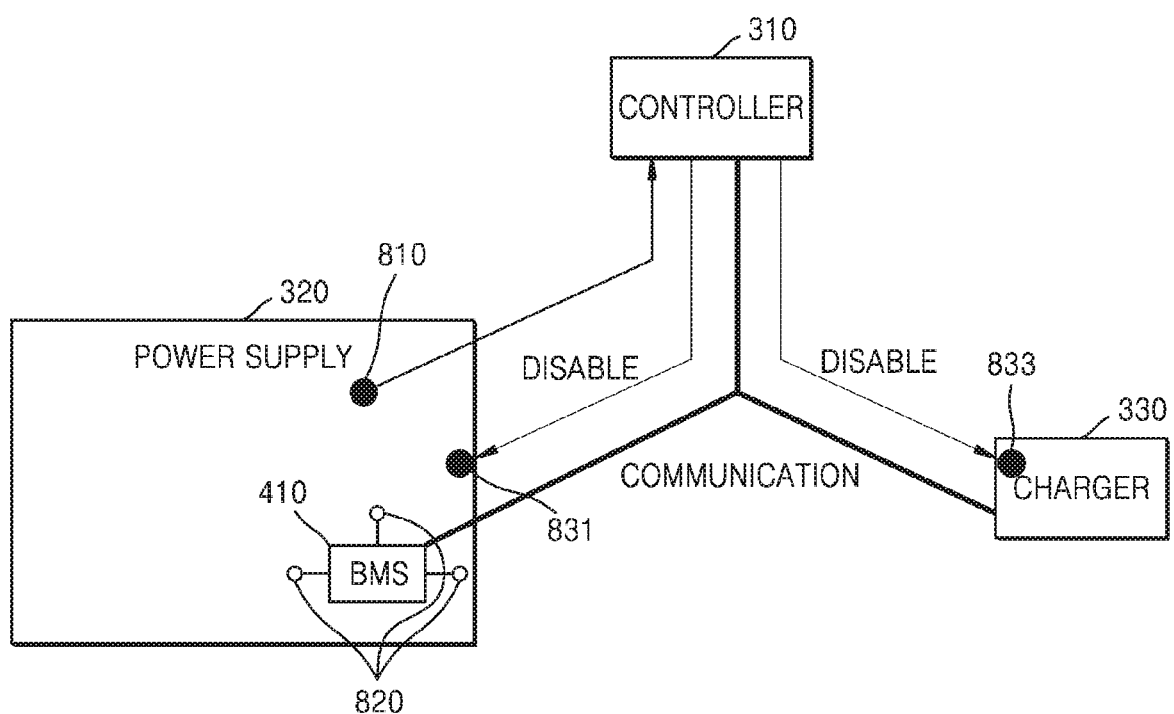
FIG. 8 illustrates a shutdown process performed by a mobile X-ray apparatus according to an embodiment.

FIG. 8 illustrates a shutdown process performed by the mobile X-ray apparatus 100 according to an embodiment. The shutdown process will now be described with reference to FIGS. 7 and 8.

Referring to FIGS. 7 and 8, the power supply 320, the controller 310, and the charger 330 may each include a communication interface and communicate with one another via their communication interfaces. For example, the power supply 320, the controller 310, and the charger 330 may communicate with one another according to a CAN protocol.

The power supply 320 may include a first temperature sensor 820.

According to an embodiment, the power supply 320 may include the first temperature sensor 820 that is dedicated for use with the battery management system (BMS) 410 and may be directly monitored by the battery management system (BMS) 410. The battery management system (BMS) 410 may use the first temperature sensor 820 to monitor a temperature of the power supply 320 and determine whether the power supply 320 is overheated. For example, if the power supply 320 is overheated to a temperature higher than a specific threshold value, the battery management system (BMS) 410 may control the charge FET 440 that is a charge controller and the discharge FET 430 that is a discharge controller to cut off a charge path and a discharge path and control a protection circuit to turn off the battery management system (BMS) 410 itself.

Furthermore, the power supply 320 may further include a second temperature sensor 810. According to an embodiment, the power supply 320 may include the second temperature sensor 810 that is dedicated for use with the controller 310 and may be directly monitored by the controller 310. The second temperature sensor 810 may be provided on outside of the battery management system (BMS) 410. If a communication error occurs between the controller 310 and the battery management system (BMS) 410, the controller 310 may not be able to receive temperature information of the power supply 320 from the battery management system (BMS) 410. In this case, the controller 310 may monitor the temperature of the power supply 320 via the second temperature sensor 810. Thus, when a communication error occurs, the controller 310 may determine whether to turn off the power supply 320 by using the second temperature sensor 810 regardless of the state of the battery management system (BMS) 410.

The power supply 320 and the charger 330 may respectively include interrupt pins 831 and 833 that can be directly controlled by the controller 310. In other words, the controller 310 may respectively transmit disable signals to the power supply 320 and the charger 330 via the interrupt pins 831 and 833, and accordingly turn off the power supply 320 and the charger 330. Thus, when it is determined that a temperature of the power supply 320 is equal to or higher than a specific threshold value via the second temperature sensor 810, the controller 310 may forcibly turn off the power supply 320 and the charger 330 via the interrupt pins 831 and 833, respectively.

Furthermore, when the battery management system (BMS) 410 operates a shutdown circuit that is a protection circuit to turn itself off, a shut down signal from the battery management system (BMS) 410 may be transmitted to the controller 310. After receiving the shut down signal, the controller 310 may monitor whether the battery management system (BMS) 410 is shut down for a specific amount of time. If the battery management system (BMS) 410 is not shut down for the specific amount of time as a result of monitoring, the controller 310 may forcibly turn off the battery management system (BMS) 410 via the interrupt pin 831. For example, after the battery management system (BMS) 410 activates a shutdown bit, the controller 310 may monitor whether the battery management system (BMS) 410 is shut down for ten (10) seconds. If the battery management system (BMS) 410 is not shut down for 10 seconds, the controller 310 may forcibly turn off the battery management system (BMS) 410 via the interrupt pin 831.

Figure 9:
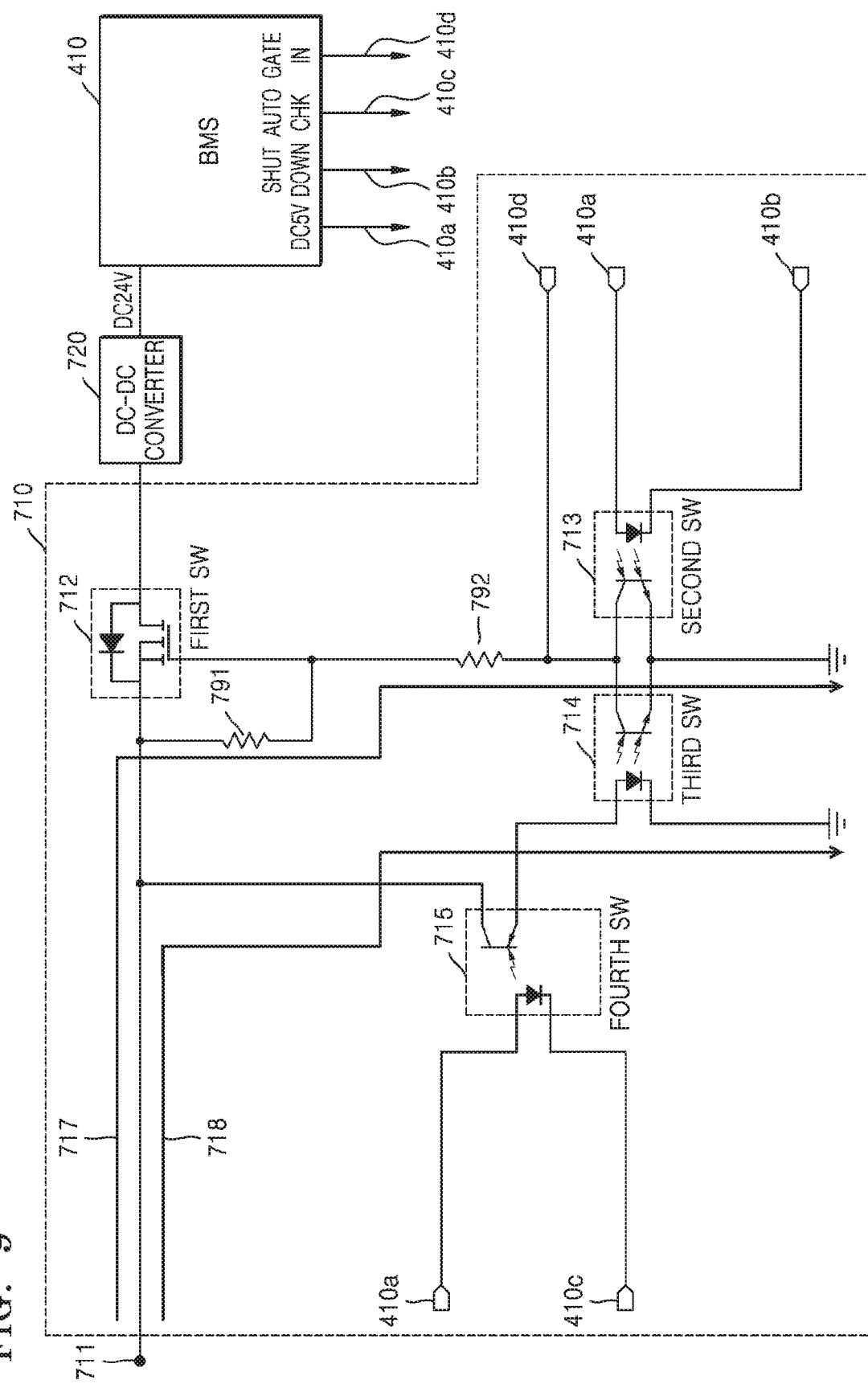
FIGS. 9 and 10 illustrate shut down circuits and neighboring elements according to embodiments.
Figure 10:
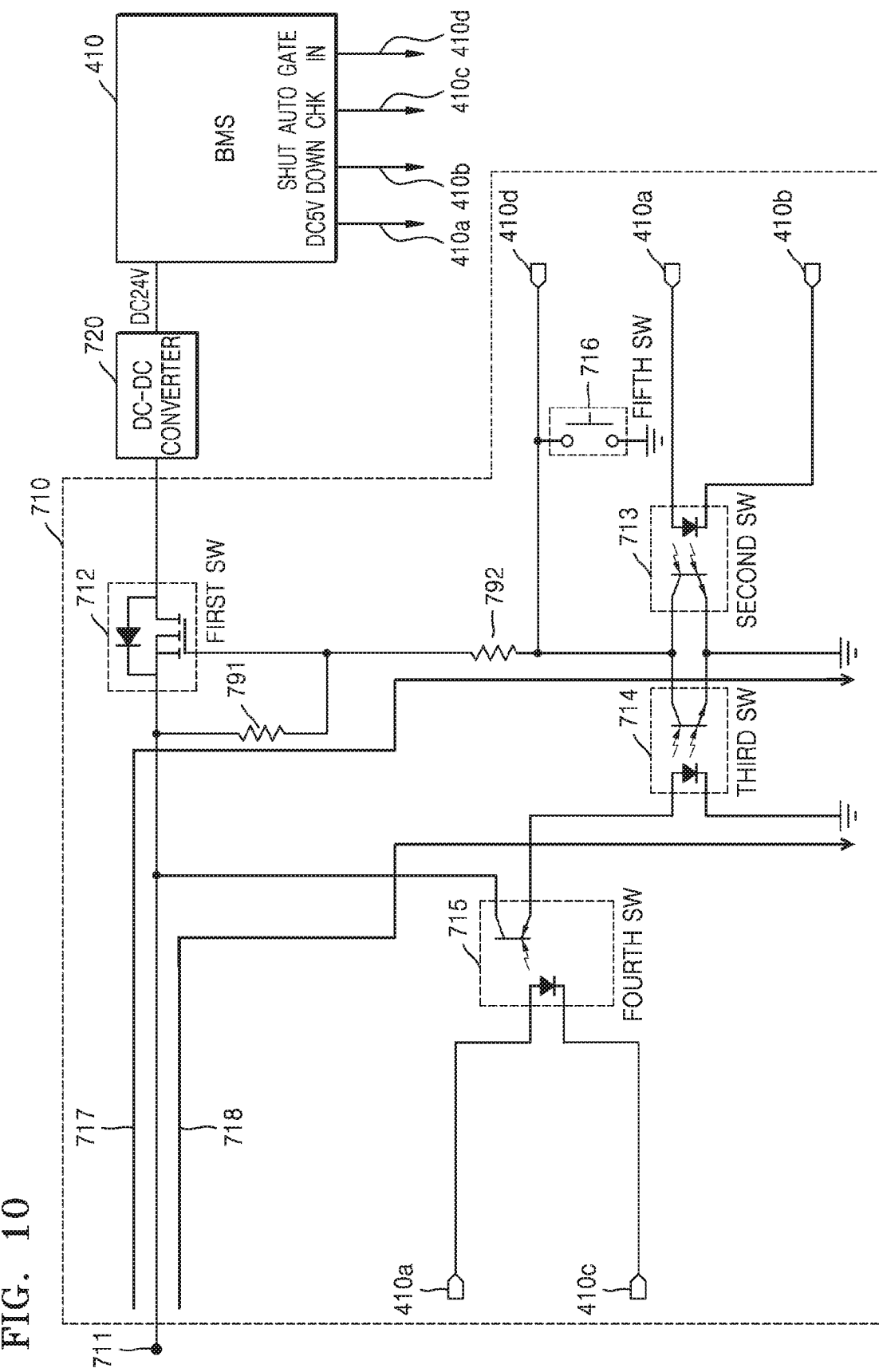

FIGS. 9 and 10 illustrate shut down circuits and neighboring elements according to embodiments.

FIG. 9 shows a shutdown circuit 710, a DC-DC converter 720, and a battery management system (BMS) 410.

Referring to FIG. 9, the shutdown circuit 710 may include first through fourth switches 712 through 715.

The first switch 712 may be implemented using a relay switch, a FET, or another switching device. The first switch 712 may prevent power from being input to the DC-DC converter 720.

For example, the first switch 712 may be constituted by a FET and be turned on or off by a voltage applied to a gate terminal. When the battery management system (BMS) 410 operates normally, the first switch 712 may be turned on or off by a first signal 410*b*, a second signal 410*c*, and/or a third signal 410*d* that is/are output from the battery management system (BMS) 410.

The second switch 713 may be driven by a DC power 410*a* output from the battery management system (BMS) 410 and may be turned on or off based on the first signal 410*b*. The first switch 712 may be turned on when the second switch 713 is turned on and be turned off when the second switch 713 is turned off. The first signal 410*b* may be a shut down signal output from the battery management system (BMS) 410 and for shutting down the battery management system (BMS) 410. The second switch 713 may be turned off when the battery management system (BMS) 410 is shut down. For example, the second switch 713 may be implemented as a photocoupler, but is not limited thereto.

The third switch 714 may operate regardless of an operation of the battery management system (BMS) 410, and may be turned on by power being supplied from the charger (330 of FIG. 7) when the battery management system (BMS) 410 is shut down. For example, the third switch 714 may be formed as a photocoupler but is not limited thereto.

The fourth switch 715 may remain in the on-state in the absence of a driving power and have one terminal connected to the third switch 714 to control an operation of turning on or off the third switch 714. When the fourth switch 715 is turned on, the third switch 714 may also be turned on. When the fourth switch 715 is turned off, the third switch 714 may also be turned off. The fourth switch 715 may be driven by the DC power 410*a* output from the battery management system (BMS) 410. For example, the fourth switch 715 may be formed as a photocoupler but is not limited thereto.

When operating normally, the battery management system (BMS) 410 may output the DC power 410*a* and the first through third signals 410*b* through 410*d*.

The DC power 410*a* may be a driving power for operating the first through fourth switches 712 through 715.

The first signal 410*b* is a shut down signal for shutting down the battery management system (BMS) 410 and is coupled to one terminal of the second switch 713 to control an on or off state of the second switch 713. For example, if the battery management system (BMS) 410 operates normally, the first signal 410*b* may remain in a logic low state to turn on the second switch 713. If the battery management system (BMS) 410 is shut down, the first signal 410*b* may change to a logic high state to turn off the second switch 713.

The second signal 410*c* is coupled to one terminal of the fourth switch 715 and may turn off the fourth switch 715 when it is in a logic low state.

The third signal 410*d* is coupled to the gate terminal of the first switch 712 and may turn on the first switch 712 when it is in a logic low state.

The shutdown circuit 710 may shut down the battery management system (BMS) 410 by preventing power from being input to the DC-DC converter 720 in response to the third signal 410*d* output from the battery management system (BMS) 410. When the battery management system (BMS) 410 is shut down, power is prevented from being supplied to the battery management system (BMS) 410, and accordingly the battery management system (BMS) 410 may be turned off.

An operation of the shutdown circuit 710 when the battery management system (BMS) 410 operates normally is now described.

During normal operation, the battery management system (BMS) 410 may output the first signal 410*b* in a logic low state and the second signal 410*c* in a logic high state.

The DC power 410a may be applied to one terminal of the second switch 713, and the first signal 410b that is in a logic low state may be applied to the other terminal thereof, so that the second switch 713 may be turned on. When the battery management system (BMS) 410 operates normally, the second switch 713 may turn on or off the first switch 712.

As the second switch 713 is turned on, a current path 717 is formed. Furthermore, since a lower voltage is applied to the gate terminal of the first switch 712 than to a source terminal due to the presence of resistors 791 and 792, the first switch 712 is turned on, and power applied to a terminal 711 may be supplied to the battery management system (BMS) 410 via the DC-DC converter 720.

In addition, the fourth switch 715 may be turned on in the absence of the DC power 410a. The fourth switch 715 may be turned off when the DC power 410a is applied and then the second signal 410c in a logic low state is applied. When the fourth switch 715 is turned off, current cannot flow into a control terminal of the third switch 714, and thus the third switch 714 may be turned off. In other words, when the battery management system (BMS) 410 operates normally, the first switch 712 may be controlled by the DC power 410a and control signals, i.e., the first through third signals 410b through 410d to remain in the on-state.

An operation of shutting down the battery management system (BMS) 410 under abnormal conditions is now described.

When overcharge, over-discharge, or overheating of a battery is detected, the battery management system (BMS) 410 may output the first signal 410b in a logic high state and shut down the battery management system (BMS) 410 itself, i.e. by preventing power from being supplied thereto.

As the first signal 410b changes from a logic low state to a logic high state, the second switch 713 is turned off. When the second switch 713 is turned off, the gate terminal of the first switch 712 is open, so the first switch 712 is turned off to prevent power from being supplied to the DC-DC converter 720 and to the battery management system (BMS) 410. Accordingly, the battery management system (BMS) 410 is shut down.

When the battery management system (BMS) 410 is shut down, the DC power 410a for driving the second through fourth switches 713 through 715 and the first through third signals 410b through 410d are not output.

A process of waking up the battery management system (BMS) 410 after shutdown is now described. A wakeup operation may mean supplying power so as to normally operate the battery management system (BMS) 410. After the battery management system (BMS) 410 is shut down, a discharge path for a battery is cut off, so that power is not supplied from the battery.

In this case, when the AC power cord (750 of FIG. 1A) is connected to an outlet (not shown) in order to normally operate the battery management system (BMS) 410, power may be applied to the terminal 711 via the charger 330.

When the fourth switch 715 is turned on and power is applied to the terminal 711 after the battery management system (BMS) 410 is shut down, power is applied to the third switch 714 via the resistors 791 and 792 to create a current path 718. The third switch 714 may then be turned on to create the current path 717. As the current paths 717 and 718 are formed, power is applied to the gate terminal of the first switch 712 via the resistor 791, and the first switch 712 is turned on. When the first switch 712 is turned on, power is applied to the battery management system (BMS) 410 via the DC-DC converter 720, and the battery management system (BMS) 410 is able to operate normally. In other words, when power is supplied to the power supply 320 via the charger 330 by connecting the AC power cord 750 when the battery management system (BMS) 410 is shut down, the battery management system (BMS) 410 may be automatically turned on.

FIG. 10 illustrates a shutdown circuit 710 and neighboring elements according to an embodiment.

In detail, FIG. 10 shows the shutdown circuit 710, a DC-DC converter 720, and a battery management system (BMS) 410.

Referring to FIG. 10, the shutdown circuit 710 may include first through fifth switches 712 through 716.

Descriptions of operations of the first through fourth switches 712 through 715 that are already provided with respect to FIG. 9 are omitted, and only an operation of the fifth switch 716 is now described.

The shutdown circuit 710 may include the fifth switch 716. The fifth switch 716 may be a physical switch, and as the fifth switch 716 operates, the battery management system (BMS) 410 may operate in the same way as described with reference to FIG. 9. For example, the fifth switch 716 may be a push switch that may turn on or off when pressed by the user.

The fifth switch 716 may be provided on outside of the main body (101 of FIG. 1A) and be pressed by the user.

The fifth switch 716 may wake up the battery management system (BMS) 410 that is shut down.

The fifth switch 716 formed as a push switch has one terminal connected to a gate terminal of the first switch 712 via the resistor 792 and the other terminal connected to a ground. If the user connects the AC power cord (750 of FIG. 1A) to an outlet (not shown) when the battery management system (BMS) 410 is shut down, power may then be applied to the terminal 711 while one terminal of the fifth switch 716 may be grounded when pressed by the user, thereby forming a current path 717. As the current path 717 is formed, a voltage drop may occur at the gate terminal of the first switch 712 to turn on the first switch 712, so that power may be supplied to the battery management system (BMS) 410. The fifth switch 716 may protrude outward from the main body 101 of the X-ray apparatus 100, and the user may wake up the X-ray apparatus 100 by operating the fifth switch 716 when the battery management system (BMS) 410 is shut down.

Conventionally, when a battery management system (BMS) is shut down after cutting off a charge path and a discharge path, an X-ray apparatus may not operate due to safety concerns. In this case, even if power is applied from outside a main body of the X-ray apparatus, the shutdown battery management system (BMS) cannot be woken up by the power so that current does not flow through a charge path and a discharge path and consequently the X-ray apparatus may fail to operate. However, according to the present embodiment, a battery management system (BMS) that is shut down may be woken up by connecting an AC power cord provided on a main body to an outlet, and an X-ray apparatus may accordingly operate. Furthermore, according to the present embodiment, it is possible to wake up the shutdown battery management system (BMS) by pressing a switch provided on the main body.

While one or more embodiments have been described with reference to the figures, it will be understood by those of ordinary skill in the art that various changes in form and details may be made therein without departing from the spirit and scope of the present disclosure as defined by the following claims. Accordingly, the above embodiments and all aspects thereof are examples only and are not limiting.

What is claimed is:

1. A mobile X-ray apparatus comprising:
   an X-ray radiator configured to emit X-rays;
   a battery configured to supply power to the X-ray radiator;
   a battery management system comprising a battery stack monitor circuit that is configured to monitor a condition of the battery and to be shut down based on the monitored condition of the battery; and
   a controller configured to receive a shutdown signal from the battery management system, monitor a current status of the battery management system for a predetermined time period, and turn off the battery management system based on the monitored current status of the battery management system.

2. The mobile X-ray apparatus of claim 1, wherein the controller is further configured to monitor at least one of a voltage, a current, and a temperature of the battery.

3. The mobile X-ray apparatus of claim 1, wherein the controller is further configured to turn off the battery management system if the battery management system is not shut down for the predetermined time period.

4. The mobile X-ray apparatus of claim 1, further comprising a charger configured to supply power to the battery and the battery management system,
   wherein the battery management system is further configured to be woken up by the power that is supplied from the charger when the battery management system is turned off.

* * * * *